United States Patent
Das et al.

(10) Patent No.: US 9,575,073 B2
(45) Date of Patent: Feb. 21, 2017

(54) DETECTION OF HIGH-RISK INTRADUCTAL PAPILLARY MUCINOUS NEOPLASM AND PANCREATIC ADENOCARCINOMA

(71) Applicant: University of Medicine and Dentistry of New Jersey, Somerset, NJ (US)

(72) Inventors: Kiron M. Das, Basking Ridge, NJ (US); Koushik K. Das, Boston, MA (US); Mari Mino-Kenudson, Burlington, MA (US)

(73) Assignees: RUTGERS, THE STATE UNIVERSITY OF NEW JERSEY, New Brunswick, NJ (US); MASSACHUSETTS GENERAL HOSPITAL, Boston, MA (US)

(*) Notice: Subject to any disclaimer, the term of this patent is extended or adjusted under 35 U.S.C. 154(b) by 556 days.

(21) Appl. No.: 13/648,921

(22) Filed: Oct. 10, 2012

(65) Prior Publication Data
US 2013/0109035 A1    May 2, 2013

Related U.S. Application Data

(60) Provisional application No. 61/545,405, filed on Oct. 10, 2011.

(51) Int. Cl.
*G01N 33/53* (2006.01)
*G01N 33/574* (2006.01)
*G01N 33/68* (2006.01)

(52) U.S. Cl.
CPC .... *G01N 33/6893* (2013.01); *G01N 33/57438* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,816,567 A | 3/1989 | Cabilly et al. | |
| 5,565,332 A | 10/1996 | Hoogenboom et al. | |
| 5,641,870 A | 6/1997 | Rinderknecht et al. | |
| 5,733,743 A | 3/1998 | Johnson et al. | |
| 5,869,046 A | 2/1999 | Presta et al. | |
| 5,871,907 A | 2/1999 | Winter et al. | |
| 5,872,215 A | 2/1999 | Osbourne et al. | |
| 5,885,793 A | 3/1999 | Griffiths et al. | |
| 5,888,743 A * | 3/1999 | Das | G01N 33/57407 435/7.1 |
| 5,962,255 A | 10/1999 | Griffiths et al. | |
| 6,140,471 A | 10/2000 | Johnson et al. | |
| 6,225,447 B1 | 5/2001 | Winter et al. | |
| 6,291,650 B1 | 9/2001 | Winter et al. | |
| 6,492,160 B1 | 12/2002 | Griffiths et al. | |
| 6,521,404 B1 | 2/2003 | Griffiths et al. | |
| 6,544,731 B1 | 4/2003 | Griffiths et al. | |
| 6,555,313 B1 | 4/2003 | Griffiths et al. | |
| 6,582,915 B1 | 6/2003 | Griffiths et al. | |
| 6,593,081 B1 | 7/2003 | Griffiths et al. | |
| 6,835,549 B2 * | 12/2004 | Das | A61B 5/055 435/7.23 |
| 7,229,770 B1 * | 6/2007 | Price | C07K 16/18 435/7.1 |
| 2003/0130496 A1 | 7/2003 | Winter et al. | |
| 2009/0311664 A1 * | 12/2009 | Fong | G01N 33/574 435/5 |

FOREIGN PATENT DOCUMENTS

| | | |
|---|---|---|
| EP | 404097 | 9/1996 |
| GB | 9206318 | 5/1992 |
| WO | 93/11161 | 6/1993 |
| WO | 94/25591 | 11/1994 |

OTHER PUBLICATIONS

Turner et al., J. Clin. Oncol. 2001, 19(4): 992-1000.*
Tang et al., J. Clin. Oncol. 1999, 17(6): 1710-1719.*
Krajewska et al., Prostate, 2006, 66:801-810.*
Coradini et al., Curr. Opin. Obst. Gyn. 2004, 16:49-55.*
Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Ang et al., Gastroenterology, Apr. 2008, 134(4), suppl. 1, pp. A93.*
Das et al., Laboratory Investigation, Feb. 2011, 91 (Suppl. 1), p. 358A, Abstract No. 1519.*
Ban et al., Am J Surg Pathol, 30(12): 1561-1569.*
"Antibody Engineering," ed. Borrebaeck, 1995 (Book description only).
Brennan et al., "Preparation of bispecific antibodies by chemical recombination of monoclonal immunoglobulin G1 fragments," Science, (1985) vol. 229, pp. 81-83 (Abstract only).
Carter et al., "High level *Escherichia coli* expression and production of a bivalent humanized antibody fragment," Biotechnology, (1992) vol. 10, pp. 163-167 (Abstract only).
Georgiou, et al., "Display of heterologou proteins on the surface of microorganisms: From the screening of combinatorial libraries to live recombinant vaccines," Nature Biotechnology, (1997) vol. 15, pp. 29-34.
Ginzinger D., "Gene quantification using real-time quantitative PCR: an emerging technology hits the mainstream," Exp Hematol., (2002) vol. 30, pp. 503-512 (Abstract only).
Hanes et al., "In vitro selection and evolution of functional proteins by using ribosome display," Proc. Nat. Acad. Sci., (1997) vol. 94, pp. 4937-4942.

(Continued)

*Primary Examiner* — Hong Sang
(74) *Attorney, Agent, or Firm* — Fox Rothschild LLP (57) ABSTRACT

The present invention relates to diagnostic, prognostic and clinical methods of distinguishing high-risk IPMN from more benign IPMN as well as high-grade PanIN and PDAC from low-grade PanIN with moderate sensitivity and very high specificity using Das-1 and related antibodies.

19 Claims, 6 Drawing Sheets

(56) References Cited

OTHER PUBLICATIONS

Holliger et al., "'Diabodies': Small bivalent and bespecific antibody fragments," Proc. Natl. Acad. Sci. USA, (1993) vol. 90, pp. 6444-6448.
Kabat et al., Sequences of Proteins of Immunological Interest, 5th Ed. Public Health Service, National Institutes of Health, Bethesda, Md. (1991) (Book description only).
Kieke, et al., "Isolation of anti-T cell receptor scFv mutants by yeast surface display," Protein Engineering, (1997) vol. 10, pp. 1303-1310.
Morimoto et al., "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, (1992) vol. 24, pp. 107-117 (Abstract only).
Morrison et al., "Chimeric human antibody molecules: mouse antigen-binding domains with human constant region domains," Proc. Natl. Acad. Sci. USA, (1984) vol. 81, pp. 6851-6855.
Pluckthun in the Pharmacology of Monoclonal Antibodies, vol. 113, Rosenburg and Moore eds., Springer-Verlag, New York, pp. 269-315 (1994).
Thaker V., "In situ RT-PCR and hybridization techniques," Methods Mol Biol., (1999) vol. 115, pp. 379-402 (Abstract only).
Vaughn, et al., "Human Antibodies with Sub-nanomolar Affinities Isolated from a Large Non-immunized Phage Display Library," Nature Biotechnology, (1996) vol. 14, pp. 309-314 (Abstract only).
Zapata et al., "Engineering linear F(ab')2 fragments for efficient production in *Escherichia coli* and enhanced antiproliferative activity," Protein Eng., (1995) vol. 8, pp. 1057-1062 (Abstract only).

\* cited by examiner

DETECTION OF HIGH-RISK INTRADUCTAL PAPILLARY MUCINOUS NEOPLASM AND PANCREATIC ADENOCARCINOMA

CROSS REFERENCE TO RELATED APPLICATION

This application claims priority of U.S. Provisional Application No. 61/545,405 filed on Oct. 10, 2011. The content of the application is incorporated herein by reference in its entirety.

GOVERNMENT SUPPORT CLAUSE

This invention was made with government support under Grant Numbers DK06318 and DK47673 awarded by the National Institute of Health. The government has certain rights in this invention.

FIELD OF THE INVENTION

This invention relates to diagnosis of pancreatic adenocarcinoma and related malignancies.

BACKGROUND OF THE INVENTION

Intraductal papillary mucinous neoplasms of the pancreas (IPMNs) are tumors characterized by intraductal proliferation of neoplastic mucinous cells with various degrees of cytologic atypia, which usually form papillae and lead to cystic dilatation of pancreatic ducts, forming clinically detectable masses. Since the first description of IPMN, over the past 30 years, these lesions have been recognized with increasing frequency, accounting for up to 20% of all resected pancreatic specimens in large referral centers. Similarly, a recent study of 2,832 consecutive abdominal CT scans undertaken for indications unrelated to pancreatic disease has found a prevalence of asymptomatic pancreatic cysts to be 2.6% among all comers and 8.7% among those above the age of 80.

Macroscopically, IPMN is classified into main-duct, combined, and branch-duct types based on the differential involvement of the pancreatic duct system. It has been shown that main-duct and combined type IPMNs are more likely to have invasive carcinoma compared to branch-duct type (48% and 42% vs. 11%), and subsequently, 5-year disease specific survival rates of main-duct and combined type IPMNs are significantly lower than that of branch-duct type (65% and 77% vs. 91%). Histologically, IPMN are thought to progress from low-grade dysplasia (adenoma) to intermediate- and high-grade dysplasia (carcinoma in situ) and invasive carcinoma. While the 5-year survival of patients with resected non-invasive IPMN is as high as 77-94%, invasive IPMN carries a much poorer survival of 33-43%. Given the significant difference in survival between invasive and non-invasive IPMNs as well as between main-duct and branch-duct IPMNs, clinical guidelines have been adopted to assist clinicians in determining when a lesion should be surgically resected. However, while sensitive (97-100%), these guidelines have proven to be highly non-specific (23-30%), especially among branch-duct IPMN. Given the prevalence of asymptomatic cysts in an elderly population who tend to have comorbidity, more specific tools that can segregate high-risk and malignant from low-risk lesions are warranted. In an effort to improve diagnostic accuracy, analyses of cyst fluid for genetic changes have been used and several biomarkers including Plectin-1 have been investigated. However, more specific markers of clinically high-risk lesions are needed to aid in the pre-operative diagnosis and risk stratification of patients with IPMN.

Recently, morphologic variations of IPMN have been recognized and criteria established for distinguishing IPMN into four distinct epithelial subtypes: gastric, intestinal, pancreatobiliary, and oncocytic. Similarly, invasive carcinoma arising in IPMN (invasive IPMN) has also been morphologically classified into colloid, tubular, and oncocytic carcinomas. Of those, the gastric-type (IPMN-G) comprises the majority of branch-duct IPMN, and rarely exhibits high-grade dysplasia (carcinoma in situ). Invasion is uncommon, but when it occurs, is usually of tubular type. The intestinal type (IPMN-I) that makes up the majority of the main-duct IPMN often exhibits intermediate- to high-grade dysplasia and is prone to developing invasive carcinoma. Given its propensity to involve the main duct and to develop invasive carcinoma, IPMN-I, even of intermediate grade, may warrant surgical intervention. Both pancreatobiliary and oncocytic (IPMN-O) types are rare, but typically demonstrate high-grade dysplasia and often contain invasive or minimally invasive carcinoma. Despite these efforts, there still is a need for more specific markers.

SUMMARY OF INVENTION

This invention relates to specific markers and their uses in determining the level of risk of intraductal papillary mucinous neoplasms, in the pancreas and other organs.

It provides a method of distinguishing high grade cases of pancreatic intraepithelial neoplasia (PanIN) and pancreatic ductal adenocarcinoma from lower grade cases. In one embodiment, the present invention provides a method of diagnosing and evaluating surgically or endoscopically resected pancreatic tissue using mAb Das-1 for establishing a pathologic diagnosis/grading of IPMN, PanIN, or invasive IPMN/pancreatic ductal adenocarcinoma. In another embodiment, the present invention provides a method of determining the malignant potential of a pancreatic cyst using mAb Das-1 to perform diagnostic evaluation of surgically or endoscopically obtained cyst fluid and perform preoperative or perioperative evaluation of the cyst. In a further embodiment, the present invention provides the use of mAb Das-1 in the serologic evaluation of patients with pancreatic cyst lesions to determine their malignant potential as well as those with increased risk of PDAC.

More specifically, in one aspect, the invention features a method for determining whether a subject has, or is at risk of having, high-risk intraductal papillary mucinous neoplasm (IPMN), high grade pancreatic intraepithelial neoplasia (PanIN), or pancreatic ductal adenocarcinoma (PDAC). The method includes, among others, (i) contacting a pancreatic tissue sample from a subject suspected of having high-risk IPMN, high grade PanIN, or PDAC with a Das-1 antibody (or antibody Das-1) or an antigen binding portion thereof; (ii) detecting immunoreactivity between the pancreatic tissue and the antibody, the presence of the immunoreactivity indicating a positive diagnosis of high-risk IPMN, high grade PanIN, or PDAC, and (iii) identifying the sample or the subject as having, or being at risk of having, high-risk IPMN, high grade PanIN, or PDAC if there is immunoreactivity between the pancreatic tissue and the antibody.

In a second aspect, the invention provides a method for diagnosing or grading IPMN, PanIN, or PDAC. The method includes (i) contacting a pancreatic tissue sample from a subject suspected of having IPMN, PanIN, or PDAC with a Das-1 antibody (or antibody Das-1) or an antigen binding portion thereof; (ii) detecting immunoreactivity between the pancreatic tissue and the antibody to obtain a level of the immunoreactivity; (iii) comparing the level of the immunoreactivity with a predetermined level; and (iv) classifying the subject with an elevated level of the immunoreactivity as having IPMN, PanIN, or PDAC.

In a third aspect, the invention provides a method for determining the malignant potential of a pancreatic cyst. This method includes (i) contacting a pancreatic cyst fluid sample from a pancreatic cyst of a subject with a Das-1 antibody (or antibody Das-1) or an antigen binding portion thereof; (ii) detecting immunoreactivity between the sample and the antibody, the presence of the immunoreactivity indicating that the pancreatic cyst is malignant; (iii) identifying the pancreatic cyst or the subject as having, or being at risk of having, malignant pancreatic cyst if there is immunoreactivity between the pancreatic tissue and the antibody.

In yet another aspect, the invention provides a method of assessing pancreatic cancer prognosis in a subject. The method includes (i) contacting a pancreatic tissue sample from a subject with a Das-1 antibody or an antigen binding portion thereof; (ii) detecting immunoreactivity between the pancreatic tissue and the antibody to obtain a level of the immunoreactivity; (iii) comparing the level of the immunoreactivity with a predetermined level; and (iv) classifying the subject as having a good prognosis if the level of the immunoreactivity decreases after receiving a treatment or as having a poor prognosis if the level of the immunoreactivity level fails to increase after receiving the treatment.

In the above-mentioned methods, the level of the immunoreactivity can be a number or percentage of cells positive for the immunoreactivity or an expression level of the antibody Das-1-binding antigen.

In the methods, the identifying or classifying step can further include generating, or otherwise communicating to a third person, a report specifying that the pancreatic tissue sample or the subject has, or is at risk of having, high-risk IPMN, high grade PanIN, or PDAC, or, for the prognosis method, that the subject under a treatment has a good or poor prognosis. The detecting step can further include obtaining a level of the immunoreactivity, and comparing the level to a predetermined level. The predetermined level can be that of a corresponding level from a normal individual or tissue that does not have the above-mentioned disorders. For the prognosis method, the predetermined level can be a level obtained from the subject at a different point of time during his or her treatment, e.g., prior to the treatment. The detecting step can be performed by various assays including, but not limited to, immunoblot, immunohistochemistry, immunocytochemistry, immunoperoxidase staining, immunofluorescence, immunoelectronmicroscopy, or ELISA. In one example, the detecting step is performed by immunoperoxidase staining. The above-mentioned methods can further include performing (i) a negative control assay on a negative control sample to detect an antibody Das-1-binding antigen in the negative control sample or (ii) a positive control assay on a positive control sample to detect an antibody Das-1-binding antigen in the positive control sample. The methods can further include, before the contacting step, obtaining the pancreatic tissue sample from the subject. Also, the methods can further include conducting a histology examination of the tissue sample.

In the methods mentioned above, the antibody can be selected from the group consisting of a monoclonal antibody, a polyclonal antibody, a multispecific antibody, an antibody fragment, a recombinant antibody, and a chemically modified antibody. The antibody or portion thereof can be directly or indirectly attached to a detectable label. The antibody fragment can be Fab, F(ab')$_2$, scFv, Fv, Fab/c, a digestion product of an antibody using a proteolytic enzyme, or an antibody prepared using a recombinant DNA technique. Preferably, the antibody is a monoclonal antibody.

In the methods mentioned above, the sample can be a surgically or endoscopically resected pancreatic tissue sample. Examples of the sample include pancreatic tissue, pancreatic tumor, pancreatic cells, pancreatic cyst fluid, or pancreatic juice. The sample can be a body fluid sample (e.g., blood, serum, and plasma from the pancreas). In a preferred embodiment, the sample is selected from the group consisting of blood, serum, plasma, pancreatic cyst fluid, and pancreatic juice.

The details of one or more embodiments of the invention are set forth in the description below. Other features, objects, and advantages of the invention will be apparent from the description and from the claims.

DETAILED DESCRIPTION OF THE INVENTION

This invention is based, at least in part, on an unexpected discovery that a monoclonal antibody, Das-1, has the ability to distinguish high-risk IPMN from more benign IPMN as well as high-grade PanIN and PDAC from low-grade PanIN with moderate sensitivity, and very high specificity. For example, it was found that mAb Das-1 is essentially absent in tissue from normal pancreatic ducts, pancreatitis, and low-grade and intermediate-grade IPMN-G. In comparison, mAb Das-1 reacts strongly and specifically with tissue from intermediate & high-grade IPMN-I, high-grade IPMN-G, and IPMN-O, all at high risk of malignant transformation. In addition, it was found that mAb Das-1 is highly reactive against tissue from invasive IPMN associated tubular and colloid carcinoma. Accordingly, the antigen recognized by this antibody, colon epithelial protein (CEP), the corresponding gene and transcript can be used as biomarkers for determining whether a subject has, or is at risk of having, the above-mentioned cellular proliferative disorder or for determining a prognosis or surveillance of a patient having such a disorder.

As disclosed herein, the CEP protein was found in pancreatic tissue and cyst fluid taken from IPMNT and was used to successfully to distinguish higher grade lesions from lower grade ones. Also, it was determined that mAb Das-1 can distinguish IPMN-I and other high-risk IPMN subtypes associated with invasive IPMNT. The immunoreactivity of the mAb was further examined against tissue with IPMN-I, IPMN-G, and IPMN-O of varying grades of dysplasia as well as colloid and tubular adenocarcinomas associated with IPMN. Finally, a number of low- and high-grade IPMNT associated cyst aspirates were analyzed for the quantitative expression of CEP, the target of mAb Das-1.

Accordingly, the present invention encompasses methods of diagnosing whether a subject has, or is at risk for, one or more of the above-mentioned cellular proliferative disorders (e.g., high-risk IPMN, high-grade PanIN, and PDAC). The invention also provides for methods of screening subjects who are thought to be at risk for developing the above-mentioned disorders. Also provided are methods of determining the efficacy of therapeutic regimens for treating the disorders. The invention also encompasses various kits suitable for carrying out the above mentioned methods or assays.

Diagnosis and Prognosis Assays

The above-describe markers and related agents (e.g., antibodies and kits) can be used in determining whether a subject has, or is at risk of having, a cellular proliferative disorder mentioned above. Alternatively, they can be used for determining a prognosis of such a disorder in a subject.

Diagnostic Assays

In one aspect, the present invention relies upon the ability of mAb Das-1 to distinguish high-risk IPMN from more benign IPMN as well as high-grade PanIN and PDAC from low-grade PanIN with moderate sensitivity, and very high specificity. Accordingly, the present invention provides assays or methods of diagnosing and evaluating a biological sample, e.g., a surgically or endoscopically resected pancreatic tissue or pancreatic cyst fluid using mAb Das-1 or its equivalent for various malignancies. In particular, evaluation of mAb Das-1 in preoperative cyst fluid may be a useful tool to identify high-risk IPMN and help clinical decision-making.

More specifically, it provides the use of mAb Das-1 or its equivalent in the diagnostic evaluation and in establishing a pathologic diagnosis/grading of IPMN, PanIN, or invasive IPMN/pancreatic ductal adenocarcinoma. In one embodiment, the invention provides the use of mAb Das-1 or its equivalent in the diagnostic evaluation of surgically or endoscopically obtained pancreatic tissue/cyst fluid for assistance in preoperative or perioperative evaluation of a pancreatic cyst to determine its malignant potential. In a further embodiment, the present invention provides the use of mAb Das-1 in the serologic evaluation of patients with pancreatic cyst lesions to determine their malignant potential as well as those with increased risk of PDAC. Thereby, the invention allows one to obtain qualitative and quantitative information to determine whether a subject has or is predisposed to a cellular proliferative disorder described herein.

A subject having such a cellular proliferative disorder or prone to it can be determined based on the expression levels, patterns, or profiles of the above-described CEP gene or its products (e.g., mRNA or protein) in a test sample from the subject. In other words, the products can be used as markers to indicate the presence or absence of the disorder. Diagnostic and prognostic assays of the invention include methods for assessing the expression level of the products. For example, a relative increase in the expression level of the CEP gene or protein is indicative of presence the disorder or a risk thereof. Conversely, a lower expression level or a lack of the expression is indicative lack of the disorder or risk.

A cancer cell or a cell prone to tumorigenesis can be detected in a subject based on the presence of the CEP protein/polypeptide or a nucleic acid (e.g., mRNA) encoding the polypeptide in a test sample from the subject. Diagnostic and prognostic assays of the invention include methods for assessing the expression level of the CEP protein or nucleic acid and for identifying variations and, optionally, mutations in the sequence of the CEP protein or nucleic acid.

The presence, level, or absence of the CEP protein or nucleic acid in a test sample can be evaluated by obtaining a test sample from a test subject and contacting the test sample with a compound or an agent capable of detecting the CEP protein or nucleic acid (e.g., antibodies, ligands, mRNA probes, or genomic DNA probes). The "test sample" includes tissues, cells and biological fluids isolated from a subject, as well as tissues, cells and fluids present within a subject. The level of expression of the CEP gene can be measured in a number of ways, including measuring the amount of protein by ELISA, quantitative western blot assay or mRNA encoded by the CEP gene; measuring the amount of polypeptide encoded by the CEP gene; or measuring the activity of polypeptide encoded by the CEP gene.

The level of mRNA corresponding to the CEP gene in a cell can be determined both by in situ and by in vitro formats. Messenger RNA isolated from a test sample can be used in hybridization or amplification assays that include, Southern or Northern analyses, PCR analyses, and probe arrays. One preferred diagnostic method for the detection of mRNA levels involves contacting the isolated mRNA with a nucleic acid probe that can hybridize to the mRNA encoded by the CEP gene. The probe can be a full-length CEP nucleic acid or a portion thereof, such as an oligonucleotide of at least 10 nucleotides in length and sufficient to specifically hybridize under stringent conditions to CEP mRNA or genomic DNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for detecting the level of CEP mRNA.

The level of mRNA (or cDNA prepared from it) in a sample encoded by the CEP gene can be evaluated with nucleic acid amplification, e.g., by standard PCR (U.S. Pat.

No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers.

For in situ methods, a cell or tissue sample can be prepared and immobilized on a support, such as a glass slide, and then contacted with a probe that can hybridize to genomic DNA on chromosomes or mRNA that encodes the CEP protein.

In another embodiment, the methods of the invention further include contacting a control sample with a compound or agent capable of detecting CEP mRNA, or genomic DNA, and comparing the presence of CEP mRNA or genomic DNA in the control sample with the presence of CEP mRNA or genomic DNA in the test sample.

The above-described nucleic acid-based diagnostic methods can provide qualitative and quantitative information to determine whether a subject has or is predisposed to a disease associated with aberrant CEP gene expression, e.g., pancreatic cancers described herein.

A variety of methods can be used to determine the level of CEP protein. In general, these methods include contacting an agent that selectively binds to the protein, such as an antibody, to evaluate the level of protein in a sample. Antibodies can be polyclonal, or more preferably, monoclonal. An intact antibody, or a fragment thereof (e.g., Fab or $F(ab')_2$ can also be used. In a preferred embodiment, the antibody bears a detectable label. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles by the Quantum Dot Corporation, Palo Alto, Calif.).

"Label" as used herein refers to a detectable compound or composition that is conjugated directly or indirectly to the antibody so as to generate a "labeled" antibody. The label can be detectable by itself (for example, radioisotope labels or fluorescent labels) or, in the case of an enzymatic label, can catalyze chemical alteration of a substrate compound or composition that is detectable. Antibodies of the described invention also can be modified to include an epitope tag or label, for example, for use in purification or diagnostic applications. Suitable detection means include the use of labels such as, but not limited to, radionucleotides, enzymes, coenzymes, fluorescers, chemiluminescers, chromogens, enzyme substrates or co-factors, enzyme inhibitors, prosthetic group complexes, free radicals, particles, dyes, and the like.

The detection methods can be used to detect the CEP protein in a biological sample in vitro as well as in vivo. In vitro techniques for detection of the CEP protein include ELISAs, immuocytochemistry, immuohistochemistry immunoprecipitations, immunofluorescence, EIA, RIA, and Western blotting analysis. In vivo techniques for detection of the CEP protein include introducing into a subject a labeled anti-CEP antibody. For example, the antibody can be labeled with a detectable substance as described above. The presence and location of the detectable substance in a subject can be detected by standard imaging techniques. In the latter case, human or humanized antibodies are preferred so as to minimize any side effects.

In one embodiment, a CEP protein may be used as an antigen in immunoassays for the detection of those individuals suffering from IPMN or pancreatic adenocarcinoma and such other diseases described herein. A CEP protein, polypeptide and/or peptide and the above-described antibodies of the present invention may be used in any immunoassay system known in the art including, but not limited to: radioimmunoassays, enzyme-linked immunosorbent assay, "sandwich" assays, precipitin reactions, gel diffusion immunodiffusion assays, agglutination assays, fluorescent immunoassays, protein A immunoassays and immunoelectrophoresis assays, to name but a few.

According to the present invention, monoclonal or polyclonal antibodies produced against the CEP protein, can be used in an immunoassay on samples of tissues to diagnose subjects with IPMN or pancreatic adenocarcinoma, and such other diseases described herein. The antibodies described herein may be used as the basic reagents in a number of different immunoassays to determine the presence of a CEP protein in a sample of tissue, blood or body fluid, such as pancreatic cystic fluid. Generally speaking, the antibodies can be employed in any type of immunoassay, whether qualitative or quantitative. This includes both the two-site sandwich assay and the single site immunoassay of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention. For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantified by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid containing a CEP protein to be tested is then added to the solid phase complex and incubated at 25° C. for a period of time sufficient to allow binding of any CEP protein present to the antibody specific for CEP protein. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-CEP protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantified, usually spectrophotometrically, to give an evaluation of the amount of antigen that is present in the sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-CEP protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested (either a pancreatic tissue section or a cyst fluid sample) containing a CEP protein may be used in a single site immunoassay wherein it is adhered to a solid substrate (e.g., a glass slide) either covalently or non-covalently. An unlabeled anti-CEP protein antibody is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for a CEP protein of interest.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., pancreatic cancer.

Prognosis Assays

The diagnostic methods described above can identify subjects having, or at risk of developing, a disease or disorder associated with a cellular proliferative disorder described herein. In addition, changes in expression levels and/or trends of the above-mentioned marker in a biological sample (e.g., a pancreatic tissue or cyst fluid) from a patient under a particular treatment can provide an early indication of recovery or lack thereof. For example, a further increase or persistently-altered gene expression levels of the marker indicate a poor/unfavorable/negative prognosis, i.e., lack of improvement or health decline. Conversely, a decrease in the gene expression levels of the marker indicates a good/favorable/positive prognosis. Accordingly, the marker allows one to assess post-treatment recovery of the above-mentioned disorders.

The prognostic assays described herein can be used to determine whether a subject is suitable to be administered with an agent (e.g., an agonist, antagonist, peptidomimetic, protein, peptide, nucleic acid, small molecule, or other drug candidate) to treat a disorder mentioned above. For example, such assays can be used to determine whether a subject can be administered with a chemotherapeutic agent.

Thus, also provided by this invention is a method of monitoring a treatment for a cellular proliferative disorder in a subject. For this purpose, gene expression levels of the marker disclosed herein can be determined for test samples from a subject before, during, or after undergoing a treatment. The changes in the levels and the magnitudes thereof as compared to a baseline level are then assessed. A decrease of the level after the treatment indicates that the subject can be further treated by the same treatment. For example, a relative decrease in the expression level of the marker is indicative of recovery from the disorder. Conversely, a further increase or persistent high expression level of the marker indicates a lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of conditions that are characterized by the above-mentioned disorders. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "detecting," "determining," "measuring," "assessing," and "assaying" are used interchangeably and include both quantitative and qualitative measurement, and include determining if a characteristic, trait, or feature is present or not. Assessing may be relative or absolute. The term includes any form of measurement, and includes determining if an element is present or not. "Detecting the presence of" a target or related immunoreactivity includes determining the amount/level of the target/immunoreactivity present, as well as determining whether it is present or absent. Assessing may be relative or absolute.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

A "test sample" or a "biological sample" as used herein may mean a sample of biological tissue or fluid that comprises protein or nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Das-1 Monoclonal Antibody and Related Antibodies

Das-1 monoclonal antibody (mAb Das-1) is a murine monoclonal antibody developed using a colon epithelial protein (CEP) and produced by the hybridoma deposited under ATCC accession number HB 9397. This antibody (formerly known as $7E_{12}H_{12}$, IgM isotype) reacts specifically with normal colonic epithelium. See e.g., U.S. Pat. No. 6,835,549, the content of which is incorporated by reference herein. On immunoblot/western blot, the antibody recognizes a large (>200 kDa) membrane-associated glycoprotein. Both via immunoperoxidase and immunofluorescence assays, it has been demonstrated that mAb Das-1 specifically reacts with both non-goblet and goblet cell colonic epithelium, but not with normal small intestinal enterocytes from the duodenum, jejunum, or ileum. mAb Das-1 is similarly absent from normal pancreatic, gastric, and esophageal mucosa. However, while mAb Das-1 is absent in the normal esophagus and gastric mucosa and chronic inflammatory conditions of the upper GI tracts (e.g., benign esophagitis, gastritis, and pancreatitis) in the absence of metaplasia/dysplais, it is strongly expressed in preneoplastic and intestinal-phenotypic changes of these organs. It has further been shown that mAb Das-1 is both highly sensitive and specific in the detection of both incomplete type gastric intestinal metaplasia and Barrett's esophagus, both being pre-malignant conditions.

As noted above, although the frequency of diagnosis of IPMN continues to increase, there remain few biomarkers available to distinguish benign from high-risk and malignant IPMNs in the preoperative setting. Here, it was demonstrated that mAb Das-1, a monoclonal antibody reactive to a colon specific antigen, is a potential novel biomarker to identify both high-risk and malignant IPMN lesions. Indeed, in our tissue cohort, mAb Das-1 was able to distinguish high-risk and malignant lesions with 77% sensitivity and 95% specificity compared to low-risk lesions. In addition to surgical specimens, we were able to demonstrate the specific detection of the mAb Das-1 antigen, CEP, in cyst fluid from IPMN by both ELISA and western blot analyses.

IPMN follow a classical adenoma-carcinoma sequence, progressing from low-grade and intermediate-grade dysplasia to carcinoma in situ and invasive carcinoma. We found that mAb Das-1 expression was preferentially in higher-grade lesions. While mAb Das-1 reacted with low- and intermediate-grade IPMN-G only among 0% (0/20) and 10% (2/21) of samples respectively, the antibody reacted with 60% (9/15) of IPMN-G with high-grade dysplasia. Similarly, the antibody reacted with 89% (17/19) of IPMN-I with high-grade dysplasia in comparison to 73% (19/26) of IPMN-I with intermediate-grade dysplasia. Among invasive IPMNs, staining with mAb Das-1 was equally significant, reacting with 80% (4/5) of tubular carcinomas and 100% (6/6) of colloid carcinomas. The slightly increased expression of mAb Das-1 among colloid-type versus tubular-type invasive IPMNs may be related to the recent evidence we have demonstrated that IPMN-I predominantly progress to colloid carcinoma as opposed to IPMN-G which often progress to tubular carcinoma. With regards to the performance of the immunohistochemistry assay, 50% of positive samples stained at a grade 3 level (>50% of affected glands staining positive) and the vast majority (77%) of samples stained at a grade 2 level or higher (at least 25% of affected glands staining positive).

With a specificity of detecting high-risk and malignant IPMNs of 95% in tissue samples, mAb Das-1 offers significantly improved specificity over current clinical guidelines. While highly sensitive (97-100%), these guidelines have proven to be highly non-specific (23-30%) in validation cohorts. Further studies need to be performed to evaluate if combining mAb Das-1 with high sensitivity clinical guidelines or other preoperative biomarkers may enhance the performance characteristics of this assay. Clinical difficulty particularly arises in the management of branch-duct IPMN lesions, which are often small in size, IPMN-G in morphologic subtype, and frequently associated with little invasion and fair survival. However, some studies have suggested a close to 20% 10-year risk of developing malignant transformation in branch-duct IPMN and their prognosis can be dismal once invasive cancer has developed. A few studies published in an abstract form have demonstrated that panels of microRNAs may be useful in differentiating invasive from non-invasive IPMNs. However, in order to capture high-risk or high-grade IPMN lesions before developing invasion, more sensitive (accurate) markers are warranted. mAb Das-1 may be of particular utility in distinguishing those low- and intermediate-grade branch-duct IPMN-G of limited clinical significance, from the high-grade IPMN-G/IPMN-I that carry a poorer clinical prognosis and would thus benefit from more definitive surgical management.

FNA with cytology is currently the standard practice in the analysis of pre-surgical cyst fluid samples. While highly specific in the hands of an experienced gastrointestinal cytopathologist, studies have brought into question its utility when acellular material is aspirated and expert interpretation is not available. In addition to cytology, to examine for immunoreactivity in cyst fluid is technically easy to perform by ELISA or western blot assay these standardized techniques are not operator dependent. Validation in a large cohort of benign and malignant cystic pancreatic lesions utilizing the pancreatic cyst fluid can standardize these assays and help accurate diagnosis and treatment plan.

Figure 4:
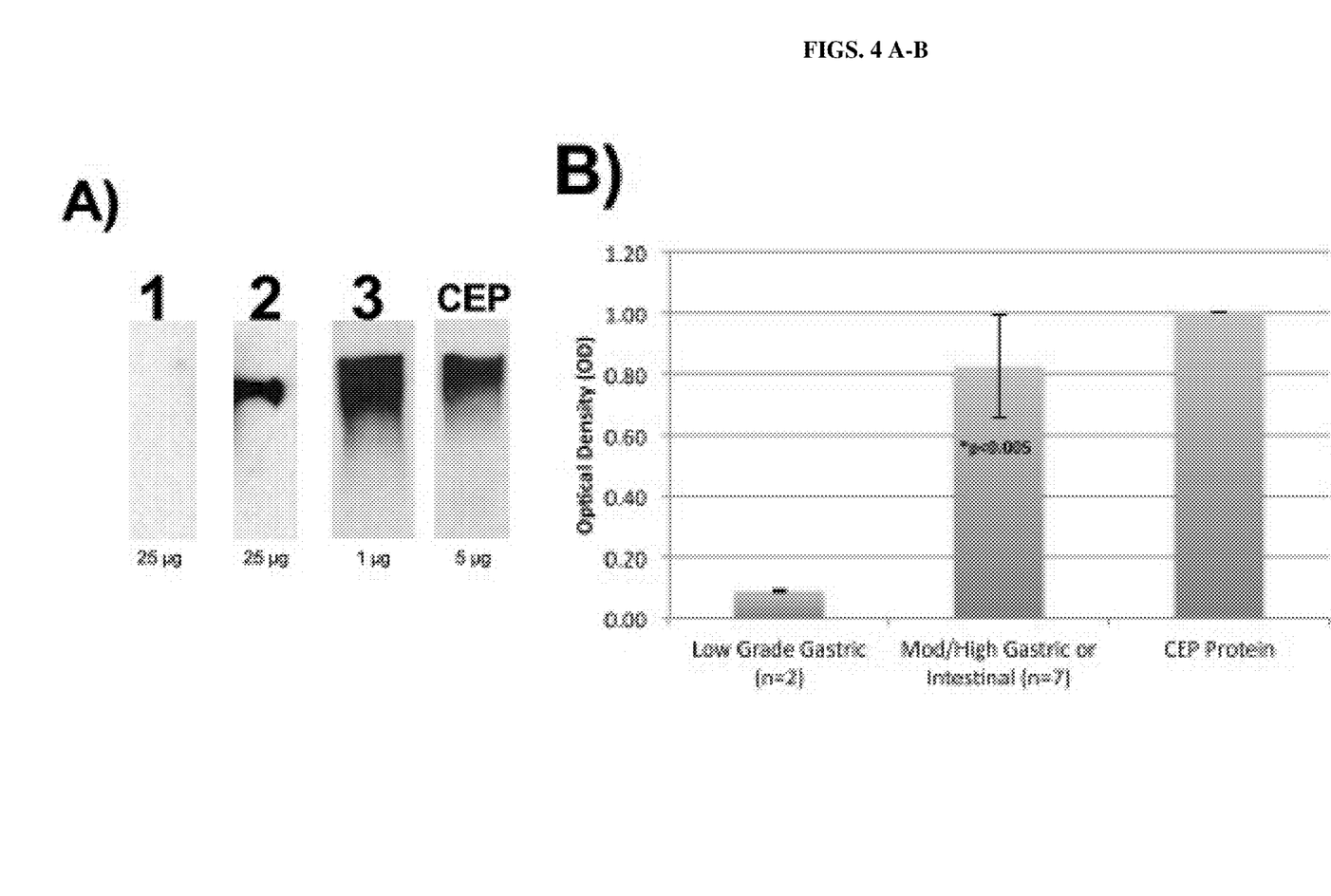
FIGS. 4A-C are a photograph and two diagrams depicting mAb Das-1 expression by western blot and ELISA analysis in pancreatic cyst fluid from highly malignant, and benign IPMN samples.

In the studies in the present invention, cyst fluid from malignant IPMNT was assayed with high reliability for mAb Das-1 using standard techniques. In fact, among IPMN-I, given the large amount of CEP protein present in the samples, fluid needed to be diluted to 1 µg to achieve an acceptable result in western blot analysis. To put this in perspective, 5 µg of purified CEP protein was required to demonstrate a similar response as a positive control (FIG. 4A). Similarly, in the ELISA assay, purified CEP protein yielded a result that was slightly less than that of IPMN-I derived cyst fluid (OD 1.004 vs 1.109) (FIG. 4C). Taken together, it is promising that even in acellular cyst fluid aspirates or limited sample materials, mAb Das-1 may still be able to be analyzed. Additionally, in contrast to cytology, it is technically easy to perform these standardized techniques and they are not operator dependent. Validation in a larger cohort of benign and malignant cystic pancreatic lesions can be performed to assess the characteristics of these assays.

Thus, mAb Das-1 is a sensitive and highly specific biomarker for the early detection of malignant IPMN. The present invention, the inclusion of mAb Das-1 into the analysis of both resected IPMN tissue as well as cyst fluid can aid in the pre-operative diagnosis and risk stratification of patients with invasive and high risk IPMN.

As mentioned above, the mAb Das-1 produced by the hybridoma deposited under ATCC accession number HB 9397 can be used to practice this invention. Other antibodies that can be used include antigen-binding portion or other variants of mAb Das-1. Thus, the term an antibody Das-1 or a Das-1 antibody includes the mAb Das-1 produced by the hybridoma deposited under ATCC accession number HB 9397 and other antibodies or antibody variants that are derived from e mAb Das-1 and have the same antigen-binding specificity. The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

It is understood in the art that an antibody is a glycoprotein having at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)). The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)).

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870. Such linear antibody fragments can be monospecific or bispecific.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291650; 6,492,160; 6,521,404; 6,544,731; 6,555,313; 6,582,915; 6,593, 081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences of the mAb Das-1 recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

Such variant antibody sequences will share 70% or more (i.e., 80%, 85%, 90%, 95%, 97%, 98%, 99% or greater) sequence identity with the sequences of the mAb Das-1 produced from the hybridoma deposited under ATCC accession number HB 9397. Such sequence identity is calculated with regard to the full length of the reference sequence (i.e., the sequence recited in the application). Percentage identity, as referred to herein, is as determined using BLAST version 2.1.3 using the default parameters specified by the NCBI (the National Center for Biotechnology Information;) [Blosum 62 matrix; gap open penalty=11 and gap extension penalty=1]. For example, peptide sequences are provided by this invention that comprise at least about 5, 10, 15, 20, 30, 40, 50, 75, 100, or more contiguous peptides of one or more of the sequences disclosed herein as well as all intermediate lengths there between. As used herein, the term "intermediate lengths" is meant to describe any length between the quoted values, such as 7, 8, 9, 10, 11, 12,13, 14, 15, 16, 17, 18, 19, etc.; 21, 22, 23, etc.; 30, 31, 32, etc.; 50, 51, 52, 53, etc.; 100, 101, 102, 103, etc.; 150, 151, 152, 153, etc.

Kits

Another purpose of the present invention is to provide kits for use in diagnostic assays for the detection of the CEP protein from individuals suspected for having or being at risk of having high-risk IPMN or pancreatic adenocarcinoma, and such other diseases described herein.

In one embodiment, the invention provides kits useful in performing diagnostic and prognostic assays using the antibodies mentioned above. Kits of the present invention include a suitable container comprising an antibody in either labeled or unlabeled form. In addition, when the antibody is supplied in a labeled form suitable for an indirect binding assay, the kit further includes reagents for performing the appropriate indirect assay. For example, the kit may include one or more suitable containers including enzyme substrates or derivatizing agents, depending on the nature of the label. Control samples (e.g., pancreatic tissue or cyst fluid from a patient known to have the above-mentioned high-risk IPMN or pancreatic adenocarcinoma) and/or instructions may also be included. The present invention also provides kits for detecting the presence of the CEP antigen or the nucleotide sequence encoding the antigen invention in a biological sample by PCR or mass spectrometry.

EXAMPLE 1

This example describes materials and methods used in EXAMPLES 2-4 below.

Study Subjects

The Massachusetts General Hospital institutional review board approved this study. A total of 271 patients with surgically resected, pathologically confirmed IPMN between January 1990 and December 2008 were identified from a prospectively collected database. Of those, 77 patients were randomly selected based on the availability of tissue blocks and in order to encompass main epithelial subtypes and all histologic grades. In this cohort, there were 108 distinct, non-invasive IPMN lesions and 11 invasive IPMNs: 26 lesions (from 25 patients) were included in a tissue microarray (TMA) that was previously prepared (see below) and 93 lesions (from 52 patients) with matched normal tissue were from whole tissue sections.

Pancreatic cyst fluid was collected from a completely separate cohort of 16 patients with benign and malignant pancreatic cysts. Fluid was aspirated peri-procedurally, during surgical resection of IPMNs (n=10), serous cystadenoma (n=1) and cystic, low-grade neuroendocrine tumor (n=1). Final diagnosis of all specimens was verified with the surgical pathologic assessment of the resected specimen. In addition, fluid from benign pancreatic pseudocysts (n=4) was obtained by routine endoscopic ultrasound and cyst aspiration.

Histologic Evaluation and Tissue Microarray Construction

All tissue samples were examined independently and classified into epithelial subtypes of IPMN on the basis of their epithelial morphology on routine H&E staining and, when available, immunoreactivity against mucin glycoproteins according to previously established criteria.[17] As for the intraductal component, there were 56 gastric-type, 45 intestinal-type, and 7 oncocytic-type epithelial lesions, but no pancreaticobiliary-type IPMN was available for examination in this series. The degree of dysplasia was independently classified into low-, intermediate-, and high-grade.

Invasive carcinomas arising in the background of IPMN were classified into: tubular adenocarcinoma (n=5) and colloid carcinoma (n=6). There was no oncocytic adenocarcinoma included in this cohort. For the purpose of this study, we classified each IPMN lesion into 2 categories based on the reported clinicopathological characteristics and prognosis of each epithelial subtype. They are low-risk IPMN consisting of low- and intermediate-grade IPMN-G lesions and high-risk and malignant IPMNs consisting of intermediate-grade IPMN-I, high-grade IPMNs of any epithelial subtypes and invasive IPMN.

Tissue microarrays were constructed from formalin-fixed, paraffin-embedded tumor containing a 2.0 mm core each of 26 lesions and 3 normal controls (resection margins of neuroendocrine tumors). The areas included on the TMA were carefully selected to ensure that representative histologic grades and epithelial subtypes were well represented. Serial 5 µm sections were obtained from all of the tissue blocks, both TMA and whole tissue. Haematoxylin-eosin (H&E) stained sections were reviewed to ensure the presence of representative lesions in the same block.

Immunohistochemistry for mAb Das-1

Tissue sections from each lesion were examined with mAb Das-1 using a sensitive immunoperoxidase assay, as described previously. In brief, tissue sections were deparaffinized by heating at 56° C. for 1 hour, immersed in xylene, rehydrated in 100%, 95%, and 70% alcohol, and finally in phosphate-buffered saline (pH 7.2). Free aldehydes were reduced with 0.05% sodium borohydride in phosphate-buffered saline (pH, 7.2) for 30 minutes at 4° C. Sections were then sequentially incubated with normal bovine serum albumin (30 minutes, 20° C.), mAb Das-1(60 minutes, 20° C.), biotinylated rabbit anti-mouse IgM (Dako; Carpinteria, Calif.) (45 minutes, 20° C.), hydrogen peroxide solution (3%) (20 minutes, 4° C.), and streptavidin-peroxidase (Dako), respectively. Tissue sections were washed in phosphate-buffered saline, treated with 3-3' diaminobenzidene hydrochloride (Dako; 10 mg in 37.5 mL of 0.5 mol/L TRIS-buffer and 30 µL of 3% hydrogen peroxide; pH, 7.2) for 30 minutes. The sections were washed, counter stained in hematoxylin or toluidine blue for 1 minute, dehydrated in graded ethanol solutions and then in xylene, and mounted for microscopic examination.

Figure 1:
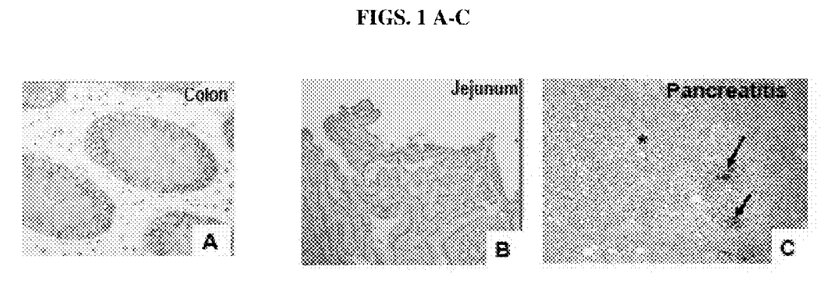
FIGS. 1A-C are a set of photographs showing immunohistochemical staining of mAb Das-1 with normal colon (A), normal jejunum (B) and invasive IPMN with associated pancreatitis (C). Strong reactivity is evident against the nests of invasive IPMN (Arrow), whereas adjacent chronic pancreatitis (*) and normal pancreatic ducts did not show any reactivity. Colonic epithelium reacts strongly with mAb Das-1 both in the cytoplasm and also along the periphery of the cells (membrane domain). Jejunal epithelium did not show any reactivity.

Each experiment also included at least two slides of normal colon and duodenal tissue sections as positive and negative controls, respectively (FIG. 1A, B). Non-neoplastic pancreatic tissue with or without IPMN related pancreatitis was available in every section and served as matched, internal controls (FIG. 1C). Reactivity to mAb Das-1 was considered positive if a crisp golden brown staining of cells was present. Two investigators (KKD and MM-K) reviewed each slide together. Samples were graded based on the percentage of affected cells that were positive: Grade 0 (negative)—<5%, Grade 1—5-25%, Grade 2—25-50%, and Grade 3—>50%. There was agreement among the investigators in all cases.

Western Blot and ELISA Analyses of Cyst Aspirate for mAb Das-1

Western blot analysis of cyst fluid was completed by standard method, as previously described with the mAb Das-1 IgM antibody. Pancreatic cyst fluid was normalized by protein amount and 25 µg was used for each sample. Given the high concentration of CEP protein, IPMN-I samples were sequentially diluted to 1 µg to allow for improved visualization of the band. Purified CEP Protein (5 µg) was run in parallel as a positive control and MOPC-IgM as a negative control. The reactivity was detected by chemi-luminescence method.

Sandwich ELISA was performed with mAb Das-1 IgM antibody and mAb Das-1 IgG isotype. Applicants have previously described the isotype switching of the mAb Das-1 IgM antibody to an IgG isotype. The ELISA plate was coated with 1 µg of mAb Das-1 IgM (anti-CEP) antibody in each well overnight at 4° C. The plate was then sequentially incubated with blocking buffer (1% normal goat serum-1% bovine serum albumin in phosphate buffer solution), 100 µg of cyst fluid samples (5 µg of purified CEP protein for positive control), 0.5 µg of mAb Das-1 IgG (anti-CEP) antibody, and alkaline phosphate conjugated anti-mouse IgG antibody, all for 1 hour at 37° C. each. Finally, phosphatase substrate solution was added into each well and optical density was detected at a wavelength of 405 nm.

Statistical Analysis

Statistical significance among tissue specimens was calculated using Fisher's Exact test, using matched, adjoining normal pancreas as internal controls. Statistical significance among cyst fluid specimens was calculated by a two tailed, heteroscedastic, student's t test. All mean values are displayed with error bars indicating standard error of the mean.

EXAMPLE 2 mAb Das-1 is Specific for High-Risk and Malignant IPMN Lesions

Of the 77 patients, 42 were male and age ranged 37-89 years (mean 68 years). The main pancreatic duct was involved by IPMN in 54 patients (10 main-duct type and 44 combined type) and the lesion was confined to branch ducts in 23. With regard to other clinicopathological features, there was no significant difference in Das-1 expression in age (p=0.446), gender (p=0.146) and type of duct involvement (branch-duct type vs. main-duct and combined type, p=0.087).

All normal pancreatic duct controls were negative for Das-1. Pancreatic parenchyma including IPMN associated pancreatitis (FIG. 1C) and stroma adjacent to IPMN lesions (FIG. 3A, starred) was also non-reactive in all the samples examined. When reactive to mAb Das-1, the lesional epithelium of IPMNs exhibited intense staining in cytoplasmic and/or membranous patterns, and no difference was observed in staining pattern, distribution, or results between tissue microarray and surgical block specimens. Using the 5% cut-off, there was not a significant difference in mAb Das-1 staining between TMA and whole tissue sections when comparing the proportion of positive samples by epithelial subtype and histologic grade (p<0.61). Overall, 62 (52%) lesions were considered positive using this cut-off.

Figure 2:
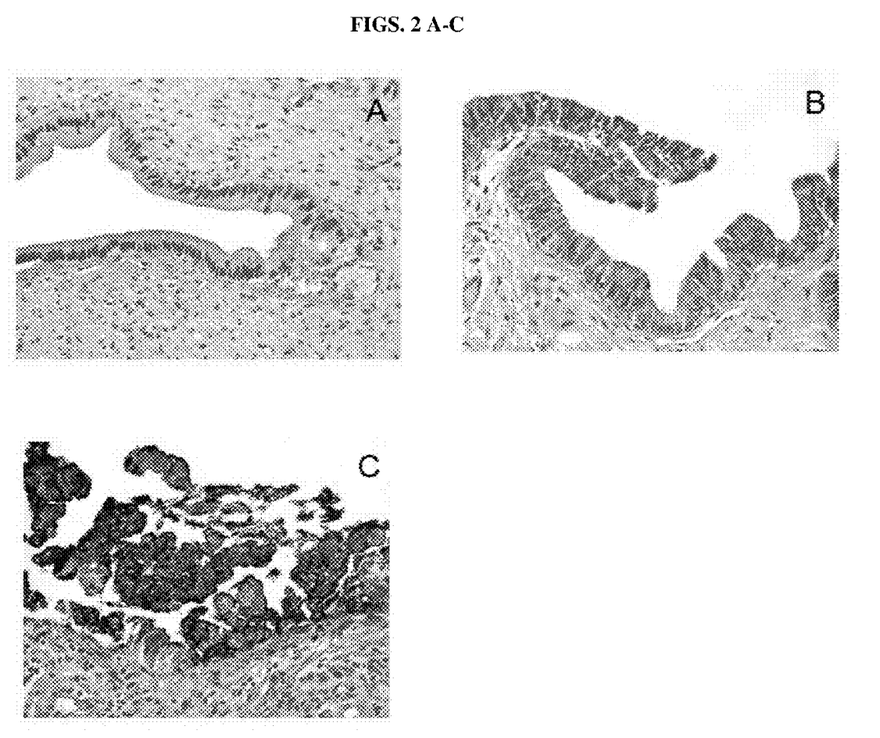
FIGS. 2A-C are a set of photographs depicting immunoperoxidase staining of mAb Das-1 against gastric-type IPMN (IPMN-G) of varying dysplasia. IPMN-G with low- (A), and intermediate-grade (B) dysplasia did not react. Whereas, IPMN-G with high-grade (C) dysplasia showed intense membranous and cytosplasmic staining.
Figure 3A:
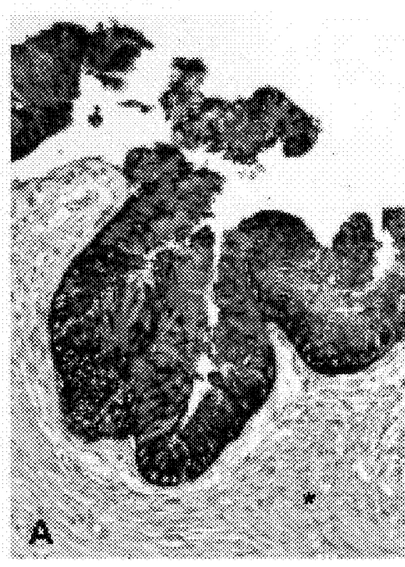
FIGS. 3A-C are a set of photographs depicting mAb Das-1 against intestinal-type IPMN (A), oncocytic-type IPMN (B), and invasive IPMN with colloid carcinoma (C). mAb Das-1 reacted strongly with both cytoplasmic and membranous staining in high grade lesions of both intestinal and oncocytic sub-types of IPMN (A & B). Among invasive IPMN with colloid carcinoma, staining was evident both in the carcinomatous cells as well as in secreted mucinous material (C).

The results of the mAb Das-1 reactivity are summarized in Table 1 below. Among IPMN-G, 0/20 (0%) lesions with low-grade dysplasia and only 2/21 (10%; Grade 1 expression: n=1, Grade 2: n=1) with intermediate-grade dysplasia were reactive to mAb Das-1. Conversely, IPMN-G with high-grade dysplasia reacted in 9/15 cases (60%; Grade 1: n=3, Grade 2: n=2, Grade 3: n=4) (FIG. 2). Compared to IPMN-G with low-or intermediate-grade dysplasia, Das-1 expression was significantly higher in IPMN-G with high-grade dysplasia (p<0.0001). Among IPMN-I, 19/26 (73%; Grade 1: n=4, Grade 2: n=5, Grade 3: n=10; p<0.0001) lesions with intermediate-grade dysplasia were positive for Das-1 as were 17/19 (89%; Grade 1: n=6, Grade 2: n=2, Grade 3: n=9; p<0.0001) with high-grade dysplasia (FIG.

Figure 3B:
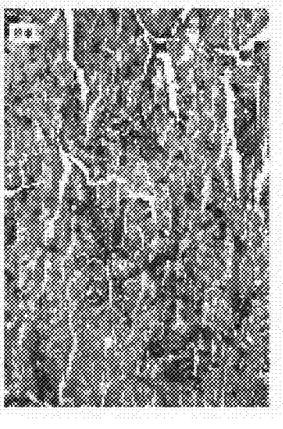

3A). IPMN-O demonstrated reactivity in 5/7 cases (71%; Grade 1: n=1, Grade 2: n=3, Grade 3: n=2; p=0.0002) (FIG. 3B).

TABLE 1 mAb Das-1 Reactivity to IPMN and invasive IPMN by Epithelial Subtype and Grade of Dysplasia

|  | IPMN-I | | IPMN-G | | | IPMN-O | INVASIVE IPMN | |
| --- | --- | --- | --- | --- | --- | --- | --- | --- |
|  | IGD* | HGD* | LGD* | IGD* | HGD* | HGD* | Tubular** | Colloid** |
| Total | 26 | 19 | 20 | 21 | 15 | 7 | 5 | 6 |
| Das-1+ | 19 | 17 | 0 | 2 | 9 | 5 | 4 | 6 |
|  | 73% | 89% | 0% | 10% | 60% | 71% | 80% | 100% |
| p-value[1] | <0.0001 | <0.0001 | NS | NS | <0.0001 | 0.0002 | 0.0004 | 0.0001 |

*IGD: intermediate-grade dysplasia, HGD: high-grade dysplasia, LGD: low-grade dysplasia
**"Tubular"—tubular adenocarcinoma; "Colloid"—colloid carcinoma
[1]Each category was compared to low- and intermediate-grade IPMNs.
Performance for High-risk IPMN Lesions: Sensitivity 77% | Specificity 95%

Figure 3C:
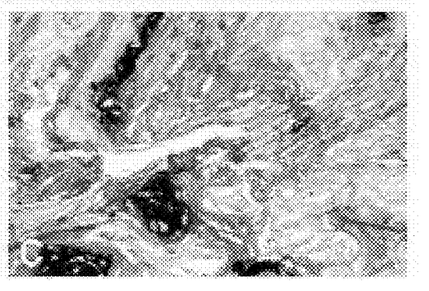

Among invasive IPMNs, mAb Das-1 was positive in 4/5 (80%; Grade 3: n=4; p=0.0004) tubular adenocarcinomas and in 6/6 (100%; Grade 2: n=3, Grade 3: n=3; p<0.0001) colloid carcinomas. Das-1 staining among invasive IPMN samples was intense, often diffuse, and mostly cytoplasmic. Interestingly, Das-1 expression was seen both in carcinomatous cells as well as in secreted mucinous material in colloid carcinomas (FIG. 3C).

Overall, the sensitivity and specificity of Das-1 in segregating high-risk and malignant IPMNs (IPMN-G with high-grade dysplasia, IPMN-I, IPMN-O and invasive IPMN) from low-risk lesions (IPMN-G with low- or intermediate-grade dysplasia) were 77% and 95%, respectively.

EXAMPLE 3

Mab Das-1 is Significantly Over-Expressed in Pancreatic Cyst Fluid from High Grade Invasive IPMNT in Comparison to Low Grade Lesions Pancreatic cyst fluid collected from low grade IPMN-G demonstrated very little reactivity to mAb Das-1 by sandwich ELISA assay (OD 0.088±0.003, n=2). In comparison, high grade IPMN lesions (moderate/high grade IPMN-G, IPMN-I, Heterogeneous IPMN with gastric and intestinal subtypes) expressed a significantly higher amount of reactivity (OD 0.824±0.167, n=7, p<0.005) (FIG. 4B). Examination of representative samples of cyst fluid by western blot analysis demonstrates a progressive increase in mAb Das-1 reactivity from low grade IPMN-G, high grade IPMN-G, and invasive IPMN-I lesions (FIG. 4A, Lanes 1, 2, 3 respectively). When examined by subtype, low grade IPMN-G (OD 0.088±0.003, n=2), moderate/high grade IPMN-G (OD 0.402±0.221, n=2), heterogeneous IPMN with gastric and intestinal subtypes (OD 0.915±0.0285, n=3), and IPMN-I (OD 1.109±0.158, n=2) demonstrated a progressive, increased reactivity to the mAb Das-1 antibody (FIG. 4C). All cyst fluid was correlated histopathologically to the associated resected surgical specimen (FIG. 4D). All experiments were normalized with respect to reactivity of the positive control, purified CEP.

EXAMPLE 4

Mab Das-1 Identified Non-IPMN Associated Pancreatic Adenocarcinoma

Figure 5:
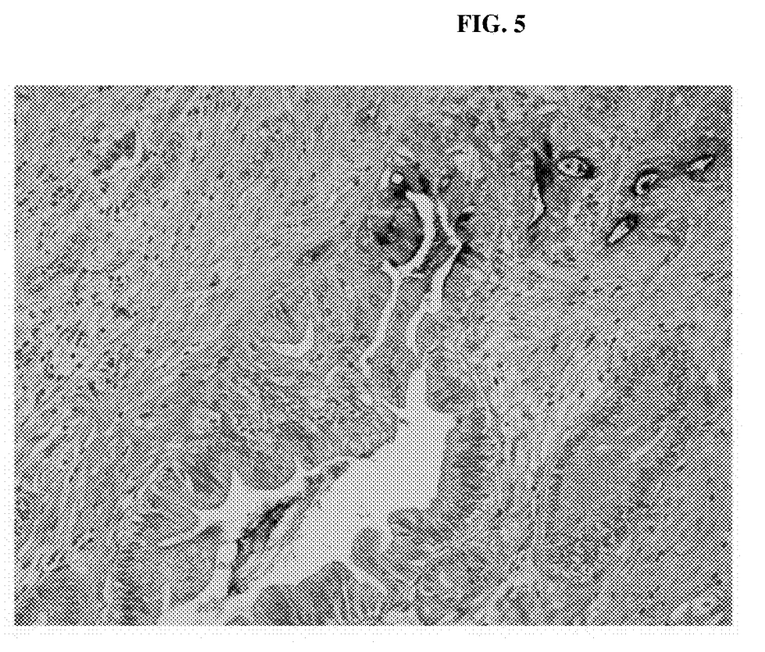
FIG. 5 is a photograph showing mAb Das-1 reacted with PANIN3 and pancreatic ductal adenocarcinoma but not low grade PANIN 1/2.
Figure 6:
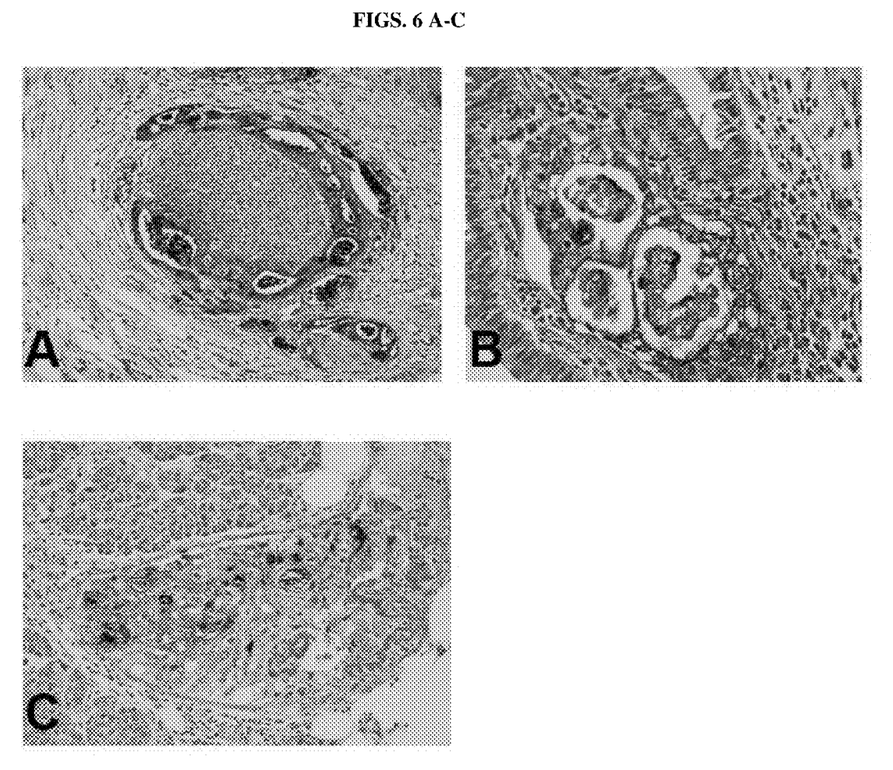
FIGS. 6A-C are a set of photographs showing that (A) positive staining of perineural involvement of adenocarcinoma; (B) positive staining of lymphatic invasion of the duodenum; and (C) positive staining of invasion of small venule with negative adjacent normal pancreas.

In this example, mAb Das-1 was used to examine samples from patients having pancreatic adenocarcinoma and associated PanIN lesions (N=84 Patients Total, Normal Matched Pancreatic Duct Control=44 Cases) using the method described above. As shown in Table 2 below, mAb Das-1 was able to distinguish high-grade PanIN and PDAC from low-grade PanIN with moderate sensitivity, and very high specificity. More specifically, it was found that mAb Das-1 reacted with PANIN3 and pancreatic ductal adenocarcinoma but not low grade PANIN 1/2 (see FIGS. 5 and 6)

TABLE 2 mAb Das-1 Reactivity to Pancreatic Adenocarcinoma and Associated PanIN lesions

|  | PANIN 1 | PANIN 2 | PANIN 3 | ADENOCA | LN |
| --- | --- | --- | --- | --- | --- |
| Total | 48 | 36 | 15 | 75 | 31 |
| + | 0 | 4 | 10 | 56 | 22 |
| % | 0 | 11 | 67 | 75 | 71 |
| FISHER EXACT TEST |  |  | 0.0002 | <0.001 | <0.001 |

*Performance for PANIN3/AdenoCa: Sensitivity 73%|Specificity 97%

In sum, the above results demonstrated that (i) mAb Das-1, a monoclonal antibody reactive to a colon specific antigen, identifies high-risk IPMN lesions with 75% sensitivity and 96% specificity compared to normal pancreatic ducts and low-risk lesions and (ii) mAb Das-1 can also identify high-grade PanIN (Pancreatic Intraepithelial Neoplasia) lesions and conventional pancreatic ductal adenocarcinoma (not arising in IPMN). The expression of this marker in preoperative samples such as cyst fluid is a useful tool to identify IPMN lesions that are malignant or at risk for malignant transformation.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method for determining whether a subject has high-risk intraductal papillary mucinous neoplasm (IPMN) of the pancreas comprising:
    contacting a pancreatic fluid sample selected from the group consisting of a pancreatic cyst fluid and pancreatic juice from a subject suspected of having high-risk IPMN with a Das-1 antibody or an antigen binding portion thereof, wherein said Das-1 antibody is produced by a hybridoma deposited under American Type Culture Collection (ATCC) accession number HB 9397; and detecting the presence or absence of immunoreactivity between the pancreatic fluid sample and the antibody or the antigen binding portion thereof, the presence of the immunoreactivity indicating a positive diagnosis of having high-risk IPMN.

2. The method of claim 1, further comprising:
identifying the subject as having high-risk IPMN if there is immunoreactivity between the pancreatic fluid sample and the antibody; and
generating a report specifying that the subject has a high-risk IPMN.

3. The method of claim 1, wherein the detecting step further comprises obtaining a level of the immunoreactivity, and comparing the level to a predetermined level.

4. The method of claim 1, wherein the detecting step is performed by immunoblot, immunohistochemistry, immunocytochemistry, immunoperoxidase staining, immunofluorescence, immunoelectronmicroscopy, Western blot,or ELISA.

5. The method of claim 4, wherein the detecting step is performed by immunoperoxidase staining.

6. The method of claim 1, further comprising performing a negative control assay on a negative control sample to detect a Das-1 antibody-binding antigen in the negative control sample.

7. The method of claim 1, further comprising performing a positive control assay on a positive control sample to detect a Das-1 antibody-binding antigen in the positive control sample.

8. The method of claim 1, wherein method further comprises, before the contacting step, obtaining the pancreatic fluid sample from the subject.

9. The method of claim 1, further comprising conducting a histology examination of the pancreatic fluid sample.

10. The method of claim 1, wherein the antibody or the antigen binding portion thereof is directly or indirectly attached to a detectable label.

11. The method of claim 10, wherein the antigen binding portion thereof, is Fab, F(ab')$_2$, scFv, Fv,Fab/c, or an antigen biding portion prepared using a recombinant DNA technique.

12. The method of claim 1, wherein the sample is pancreatic cyst fluid.

13. A method for diagnosing or grading intraductal papillary mucinous neoplasm (IPMN)of the pancreas, comprising:
contacting a pancreatic fluid sample selected from the group consisting of pancreatic cyst fluid and pancreatic juice from a subject suspected of having high-risk IPMN with a Das-1antibody or an antigen binding portion thereof, said Das-1 antibody is produced by a hybridoma deposited under America Type Culture Collection (ATCC) accession number HB 9397;

detecting the presence or absence of immunoreactivity between the pancreatic fluid sample and the antibody or the antigen binding portion thereof, to obtain level of the immunoreactivity, wherein al elevated level of the immunoreactivity compared to a pre-determined level indicates a positive diagnosis of high-risk IPMN.

14. The method of claim 13, further comprising:
comparing the level of the immunoreactivity with an predetermined level; and
classifying the subject with an elevated level of the immunoreactivity as having high-risk IPMN;
wherein the level of the immunoreactivity is a number or percentage of cells positive for the immunoreactivity, or the level of the immunoreactivity is an expression level of the Das-1 antibody-binding antigen.

15. A method of monitoring treatment response in a subject having high-risk IPMN of the pancreas comprising:
contacting a pancreatic fluid sample selected from the group consisting of pancreatic cyst fluid and pancreatic juice from a subject after receiving a treatment for high-risk IPMN of the pancreas with a Das-1 antibody or an antigen biding portion thereof, said Das-1 antibody produced by a hybridoma deposited under American Type Culture Collection (ATCC) accession number HB 9397; and
detecting change in immunoreactivity between the pancreatic fluid sample and the antibody or the antigen binding portion thereof to obtain a level of the immunoreactivity, wherein a decreased immunoreactivity level compared to the level obtained from the subject prior to the treatment indicates a good treatment response.

16. The method of claim 15, further comprising:
comparing the level of the immunoreactivity with a predetermined level, wherein the predetermined level is obtained from the subject prior to receiving the treatment;
classifying the subject as having a good treatment response if the level of the immunoreactivity decreases after receiving the treatment or as having a poor treatment response if the level of the immunoreactivity level fails to decrease after receiving the treatment; and
generating a report specifying that the subject has a good treatment response or a poor treatment response.

17. The method of claim 15, wherein the sample is pancreatic cyst fluid.

18. The method of claim 15, wherein the detection is performed by ELISA.

19. The method of claim 13, wherein the sample is pancreatic cyst fluid.

* * * * *